(12) United States Patent
Lee et al.

(10) Patent No.: US 11,974,831 B2
(45) Date of Patent: May 7, 2024

(54) APPARATUS AND METHOD FOR ESTIMATING BODY TEMPERATURE

(71) Applicant: SAMSUNG ELECTRONICS CO., LTD., Suwon-si (KR)

(72) Inventors: So Young Lee, Suwon-si (KR); Sang Kyu Kim, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 331 days.

(21) Appl. No.: 17/498,931

(22) Filed: Oct. 12, 2021

(65) Prior Publication Data

US 2023/0036809 A1    Feb. 2, 2023

(30) Foreign Application Priority Data

Jul. 29, 2021    (KR) .................. 10-2021-0099557

(51) Int. Cl.
*A61B 5/01*    (2006.01)
*A61B 5/00*    (2006.01)
(Continued)

(52) U.S. Cl.
CPC .............. *A61B 5/01* (2013.01); *A61B 5/6815* (2013.01); *G01K 13/20* (2021.01); *G01K 15/005* (2013.01); *A61B 5/6803* (2013.01); *A61B 5/681* (2013.01); *A61B 2560/0223* (2013.01); *A61B 2560/0252* (2013.01); *A61B 2562/0271* (2013.01)

(58) Field of Classification Search
CPC ....... A61B 5/01; A61B 5/6815; A61B 5/6803; A61B 5/681; A61B 2560/0223; A61B 2560/0252; A61B 2562/0271; A61B 5/0008; A61B 5/4815; A61B 5/6817; A61B 5/6898; A61B 5/015; A61B 2560/0228; G01K 13/20; G01K 15/005; G01K 7/427;

(Continued)

(56) References Cited

U.S. PATENT DOCUMENTS 8,226,294 B2    7/2012    Bieberich et al.
8,716,629 B2    5/2014    Klewer et al.
(Continued)

FOREIGN PATENT DOCUMENTS

| JP | 2014-132278 A | 7/2014 |
| WO | 2017/001701 A1 | 1/2017 |
| WO | 2017/062923 A1 | 4/2017 |

*Primary Examiner* — Eric F Winakur
*Assistant Examiner* — Jaimie Annette McKeel
(74) *Attorney, Agent, or Firm* — Sughrue Mion, PLLC

(57) ABSTRACT

An apparatus for estimating a core body temperature of an object is provided. The apparatus may include a heat flow sensor configured to measure a first heat flux from an object, a first temperature sensor positioned under a thermal conducting material and configured to measure a surface temperature of the object, a second temperature sensor positioned above the thermal conducting material and configured to measure a surface temperature of the thermal conducting material, and a processor configured to obtain a second heat flux by calibrating the first heat flux based on the surface temperature of the object and the surface temperature of the thermal conducting material, and configured to estimate a core body temperature of the object based on the obtained second heat flux and the surface temperature of the object.

13 Claims, 12 Drawing Sheets

(51) Int. Cl.
*G01K 13/20* (2021.01)
*G01K 15/00* (2006.01)

(58) Field of Classification Search
CPC ............ G01K 1/14; G01K 1/165; G01K 7/22;
G16H 50/20; G06F 1/163
See application file for complete search history.

(56) References Cited

U.S. PATENT DOCUMENTS

| | | |
|---|---|---|
| 9,220,416 B2 | 12/2015 | Blank et al. |
| 9,354,122 B2 | 5/2016 | Bieberich et al. |
| 9,699,546 B2 | 7/2017 | Qian et al. |
| 9,716,937 B2 | 7/2017 | Qian et al. |
| 10,088,373 B2 | 10/2018 | Durrer et al. |
| 10,274,383 B2 | 4/2019 | Bieberich et al. |
| 10,405,755 B2 | 9/2019 | Shrubsole et al. |
| 10,750,951 B1 * | 8/2020 | Prachar ................. G01K 13/20 |
| 10,765,409 B2 | 9/2020 | Lafon et al. |
| 10,959,942 B2 | 3/2021 | Sandvang et al. |
| 2007/0225614 A1 | 9/2007 | Naghavi et al. |
| 2016/0213354 A1 | 7/2016 | Levin et al. |
| 2016/0235306 A1 | 8/2016 | Atallah et al. |
| 2019/0285488 A1 | 9/2019 | Lundström et al. |
| 2020/0060869 A1 | 2/2020 | Telfort et al. |
| 2020/0217727 A1 | 7/2020 | Heitz et al. |
| 2020/0397305 A1 | 12/2020 | Mensch et al. |
| 2021/0123819 A1 | 4/2021 | Seyama et al. |
| 2022/0170800 A1 * | 6/2022 | Matsunaga ............ G01K 13/20 |

* cited by examiner

APPARATUS AND METHOD FOR ESTIMATING BODY TEMPERATURE

CROSS-REFERENCE TO RELATED APPLICATION(S)

This application claims priority to Korean Patent Application No. 10-2021-0099557, filed on Jul. 29, 2021, in the Korean Intellectual Property Office, the entire disclosure of which is incorporated by reference herein for all purposes.

BACKGROUND

1. Field

Example embodiments of the disclosure relate to an apparatus and a method for estimating core body temperature using a plurality of sensors.

2. Description of Related Art

In general, body temperature is one of the four basic vital signs and has very important clinical significance. A body temperature sensor may be used in various applications, such as detection of whether a patient is infected or whether there is a thermal side effect of a drug, detection or prediction of ovulation time, and the like. However, it is not easy to measure a core body temperature using a mobile device, such as a wearable device, because the skin temperature and the core body temperature may differ depending on the ambient temperature. General temperature sensors may include contact sensors and non-contact sensors. Contact sensors include sensors that detect changes in electrical resistance, such as resistance temperature detectors (RTDs) and thermistors, and thermocouples that detect electromotive force. In addition, non-contact sensors include thermopiles, microbolometers, which measure infrared rays emitted from the human body surface to measure a body temperature. A conventional body temperature measurement technique is greatly affected by changes in external ambient temperature and environmental conditions that affect heat transfer, such as humidity, air flow, and the like.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

According to an aspect of an example embodiment, provided is an apparatus for estimating a body temperature, including: a heat flow sensor configured to measure a first heat flux from an object; a first temperature sensor positioned under a thermal conducting material and configured to measure a surface temperature of the object; a second temperature sensor positioned above the thermal conducting material and configured to measure a surface temperature of the thermal conducting material; and a processor configured to obtain a second heat flux by calibrating the first heat flux based on the surface temperature of the object and the surface temperature of the thermal conducting material, and configured to estimate a core body temperature of the object based on the second heat flux and the surface temperature of the object.

The processor may be further configured to obtain a first correction coefficient based on a resistance value of the thermal conducting material, the surface temperature of the object, and the surface temperature of the thermal conducting material, and configured to calibrate the first heat flux based on the first correction coefficient.

The processor may be further configured to obtain the first correction coefficient based on a ratio between a value obtained by subtracting the surface temperature of the thermal conducting material from the surface temperature of the object and the resistance value of the thermal conducting material.

The processor may be further configured to calibrate the first heat flux by using a value obtained by multiplying the first correction coefficient and a predefined second correction coefficient.

The processor may be further configured to obtain a third heat flux based on the surface temperature of the object and the surface temperature of the thermal conducting material and configured to calibrate the first heat flux based on the third heat flux.

The processor may be further configured to obtain the third heat flux based on a value obtained by subtracting the surface temperature of the thermal conducting material from the surface temperature of the object.

The processor may be further configured to obtain the second heat flux by combining the first heat flux and the third heat flux.

The processor may be further configured to estimate the core body temperature of the object by combining the surface temperature of the object and the second heat flux, by using a predefined body temperature estimation model.

The thermal conducting material may include an insulator.

The first temperature sensor and the second temperature sensor may be a pair of thermistors.

According to an aspect of an example embodiment, provided is a method of estimating a body temperature, including: measuring, by a heat flow sensor, a first heat flux from an object; measuring, by a first temperature sensor positioned under a thermal conducting material, a surface temperature of the object; measuring, by a second temperature sensor positioned above the thermal conducting material, a surface temperature of the thermal conducting material; obtaining a second heat flux by calibrating the first heat flux based on the surface temperature of the object and the surface temperature of the thermal conducting material; and estimating a core body temperature of the object based on the second heat flux and the surface temperature of the object.

The calibrating the first heat flux may include: obtaining a first correction coefficient based on a resistance value of the thermal conducting material, the surface temperature of the object, and the surface temperature of the thermal conducting material; and calibrating the first heat flux by using the first correction coefficient.

The obtaining the first correction coefficient may include obtaining the first correction coefficient based on a ratio between a value obtained by subtracting the surface temperature of the thermal conducting material from the surface temperature of the object and the resistance value of the thermal conducting material.

The calibrating the first heat flux may include calibrating the first heat flux by using a value obtained by multiplying the first correction coefficient and a predefined second correction coefficient.

The calibrating the first heat flux may include: obtaining a third heat flux based on the surface temperature of the object and the surface temperature of the thermal conducting material; and calibrating the first heat flux based on the third heat flux.

The obtaining the third heat flux may include obtaining the third heat flux based on a value obtained by subtracting the surface temperature of the thermal conducting material from the surface temperature of the object.

The obtaining the second heat flux may include obtaining the second heat flux by combining the first heat flux and the third heat flux.

The estimating the core body temperature may include estimating the core body temperature of the object by combining the surface temperature of the object and the second heat flux by using a predefined body temperature estimation model.

According to an aspect of an example embodiment, provided is an electronic device including: a main body; and an apparatus for estimating body temperature, wherein the apparatus for estimating body temperature includes: a heat flow sensor configured to measure a first heat flux from an object; a first temperature sensor positioned under a thermal conducting material and configured to measure a surface temperature of the object; a second temperature sensor positioned above the thermal conducting material and configured to measure a surface temperature of the thermal conducting material; and a processor configured to obtain a second heat flux by calibrating the first heat flux based on the surface temperature of the object and the surface temperature of the thermal conducting material, and configured to estimate a core body temperature of the object based on the second heat flux and the surface temperature of the object.

The electronic device may be a wearable device including at least one of a smart watch, a smart band, smart glasses, a smart necklace, and an ear-type wearable device.

BRIEF DESCRIPTION OF THE DRAWINGS

The above and other aspects, features, and advantages of certain example embodiments of the disclosure will be more apparent from the following description taken in conjunction with the accompanying drawings.

DETAILED DESCRIPTION

Figure 1:
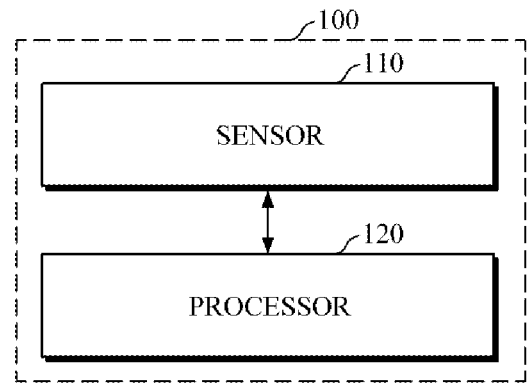
FIG. 1 is a block diagram illustrating an example of an apparatus for estimating body temperature according to an example embodiment.

Details of example embodiments are provided in the following detailed description with reference to the accompanying drawings. The disclosure may be understood more readily by reference to the following detailed description of example embodiments and the accompanying drawings.

Throughout the drawings and the detailed description, unless otherwise described, the same drawing reference numerals will be understood to refer to the same elements, features, and structures. The relative size and depiction of these elements may be exaggerated for clarity, illustration, and convenience. The disclosure may, however, be embodied in many different forms and should not be construed as being limited to the embodiments set forth herein. Rather, these embodiments are provided so that the disclosure will be thorough and complete and will fully convey the concept of the invention to those skilled in the art, and the disclosure will only be defined by the appended claims. Like reference numerals refer to like elements throughout the specification.

It will be understood that, although the terms first, second, etc. may be used herein to describe various elements, these elements should not be limited by these terms. These terms are only used to distinguish one element from another. Also, the singular forms are intended to include the plural forms as well, unless the context clearly indicates otherwise. In the specification, unless explicitly described to the contrary, the word "comprise" and variations such as "comprises" or "comprising," will be understood to imply the inclusion of stated elements but not the exclusion of any other elements. Terms such as "unit" and "module" denote units that process at least one function or operation, and they may be implemented by using hardware, software, or a combination of hardware and software.

Figure 2:
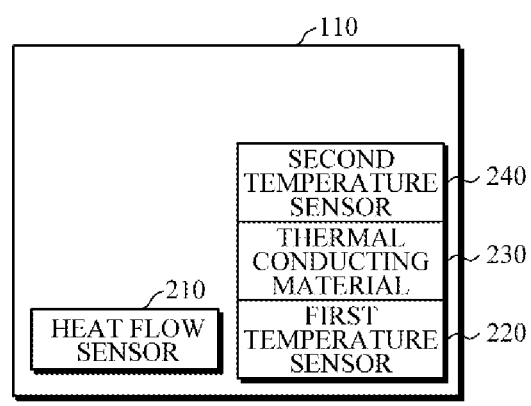
FIG. 2 is a detailed block diagram illustrating a sensor according to an example embodiment.

FIG. 1 is a block diagram illustrating an example of an apparatus for estimating body temperature according to an example embodiment. FIG. 2 is a detailed block diagram illustrating a sensor according to an example embodiment.

Referring to FIG. 1, an apparatus 100 for estimating body temperature may include a sensor 110 and a processor 120.

The sensor 110 may include a plurality of sensors configured to obtain data for estimating a core body temperature from an object, and the processor 120 may use the data obtained from the plurality of sensors to estimate a core body temperature of the object. The processor may be electrically connected to the sensor 110 and may control the sensor 110 when body temperature estimation is requested.

Referring to FIG. 2, the sensor 110 may include a heat flow sensor 210, a first temperature sensor 220, and a second temperature sensor 240. In addition, the first temperature sensor 220 and the second temperature sensor 240 may be disposed in a stacked manner with a thermal conducting material 230 interposed therebetween, and may be disposed to be spaced apart from the heat flow sensor 210.

The heat flow sensor 210 may measure a heat flux from the object. The heat flow sensor is a sensor capable of measuring a heat flux through measurement of a heat flux density and may measure the heat flux by being in contact with an object.

The first temperature sensor 220 may be positioned under the thermal conducting material 230 to measure a surface temperature of the object, and the second temperature sensor 240 may be positioned above the thermal conducting material 230 to measure a surface temperature of the thermal conducting material 230. The thermal conducting material 230 may be an insulator having, for example, a size of 0.1 to 5 mm, and may be a material (e.g., polyurethane foam) having a thermal conductivity of less than 0.1 W/mK. The size or thermal conductivity of the insulator is not limited thereto. In addition, it is also possible to fill a space between the first temperature sensor 220 and the second temperature sensor 240 using air having very low thermal conductivity without requiring an additional material. The first temperature sensor 220 and the second temperature sensor 240 may include a thermistor. A thermistor is a contact type temperature sensor for measuring a temperature, and may be placed in contact with, for example, a wrist of an object and measure a surface temperature of the wrist. In addition, the first temperature sensor 220 and the second temperature sensor 240 may be configured as a pair of thermistors having a thermal conducting material interposed therebetween. Hereinafter, a description will be given, when needed, using a thermistor pair as an example for convenience of explanation.

The processor 120 may obtain a heat flux (hereinafter referred to as a "first heat flux") measured by the heat flow sensor 210, calibrate the first heat flux based on the surface temperature of the object measured by the first temperature sensor 220 and the surface temperature of the thermal conducting material 230 measured by the second temperature sensor 240 to obtain a calibrated heat flux (hereinafter referred to as a "second heat flux"), and estimate the core body temperature of the object based on the obtained second heat flux and the surface temperature of the object.

For example, the processor 120 may calculate a correction coefficient (hereinafter referred to as a "first correction coefficient") based on the resistance value of the thermal conducting material 230, the surface temperature of the object, and the surface temperature of the thermal conducting material 230, and may calibrate the first heat flux using the calculated first correction coefficient.

Figure 3:
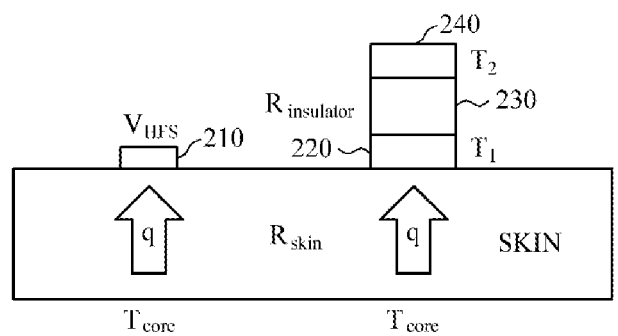
FIGS. 3 and 4 are diagrams for explaining an example of calibrating a first heat flux measured by a heat flow sensor according to an example embodiment.
Figure 4:
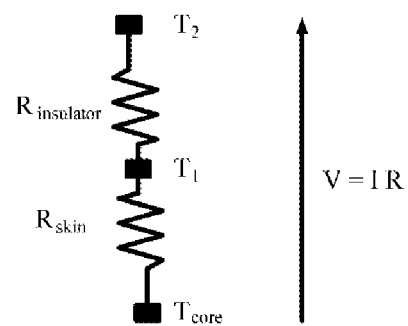

FIGS. 3 and 4 are diagrams for explaining an example of calibrating the first heat flux measured by the heat flow sensor 210.

Generally, a heat flow sensor measures a heat flux through a voltage generated by a temperature difference between both surfaces of a thermopile, and the heat flux may be expressed as a voltage. However, for the same thermal reaction, each heat flow sensor may output a different voltage, and thus a calibration between the voltage of the heat flow sensor and the heat flux is needed for accurate measurement.

Referring to FIGS. 3 and 4, a difference between a core body temperature $T_{core}$ and a skin surface temperature $T_1$ is represented as a first heat flux q, which may be measured as a voltage $V_{HFS}$ by the heat flow sensor 210. In addition, the first heat flux q may be estimated from a temperature difference $T_1-T_2$ between the first temperature sensor 220 and the second temperature sensor 240 that are disposed in the vicinity of the heat flow sensor 210 and have the thermal conducting material 230 interposed therebetween. In this case, Equation 1 may be derived by Ohm's law (V=IR) in relation to the heat transfer of the first temperature sensor 220 and the second temperature sensor 240.

$$I = \frac{T_{core} - T_1}{R_{Skin}} = \frac{T_1 - T_2}{R_{insulator}} \tag{1}$$

Here, $T_{core}$ represents the core body temperature, $T_1$ represents the surface temperature of the object, $T_2$ represents the surface temperature of the thermal conducting material, $R_{skin}$ represents the skin resistance, $R_{insulator}$ represents the resistance of the thermal conducting material, and I represents the thermal current.

The difference between the core body temperature $T_{core}$ and the surface temperature $T_1$ of the object may be expressed as Equation 2, and I in Equation 1 may be expressed as Equation 3 by using Equation 2.

$$T_{core} - T_1 = \alpha V_{HFS} \tag{2}$$

$$I = \frac{\alpha V_{HFS}}{R_{Skin}} = \frac{T_1 - T_2}{R_{insulator}} \tag{3}$$

Here, $V_{HFS}$ represents the voltage of the heat flow sensor 210, and α represents the correction coefficient of the heat flow sensor 210. Equation 3 may be further expressed as Equation 4.

$$\gamma = \frac{\alpha}{R_{Skin}} = \frac{1}{V_{HFS}} \frac{(T_1 - T_2)}{R_{insulator}} \qquad \text{[Equation 4]}$$

Here, γ represents the final correction coefficient of the heat flow sensor 210, which will be referred to as a "first correction coefficient." That is, the processor 120 may calculate the first correction coefficient based on the ratio between the value obtained by subtracting the surface temperature $T_2$ of the thermal conducting material from the surface temperature $T_1$ of the object and the resistance value $R_{insulator}$ of the thermal conducting material 230.

In addition, by using a predefined temperature estimation model, the processor 120 may perform calibration on the first heat flux by using a value obtained by multiplying the calculated first correction coefficient and a predefined core body temperature estimation correction coefficient (hereinafter referred to as a "second correction coefficient"), and may estimate the core body temperature by combining a second heat flux and the surface temperature of the object, which may be expressed by Equation 5.

$$\hat{T}_{core} = T_{skin} + \alpha V_{HFS} = T_{skin} + \beta\gamma V_{HFS} \tag{5}$$

Here, β represents the predefined second correction coefficient, $\beta\gamma V_{HFS}$ represents the second heat flux resulting from the calibration, $T_{skin}$ represents the skin surface temperature with the same value as $T_1$, and $\hat{T}_{core}$ represents a vector value.

In another embodiment, the processor 120 may obtain a third heat flux based on the surface temperature $T_1$ of the object and the surface temperature $T_2$ of the thermal conducting material, and calibrate the first heat flux based on the third heat flux.

For example, the processor 120 may obtain the third heat flux based on the value obtained by subtracting the surface temperature $T_2$ of the thermal conducting material 230 from the surface temperature $T_1$ of the object, obtain the second heat flux by combining the first heat flux and the third heat flux, and estimate the core body temperature of the object through combination of the obtained second heat flux and the skin temperature of the object by using the predefined temperature estimation model, which may be expressed by Equation 6.

$$\hat{T}_{core} = T_{skin} + \beta_{HFS} q_{HFS} + \beta_{TH} q_{TH} \tag{6}$$

Here, $q_{TH}$ represents the third heat flux obtained by subtracting the surface temperature $T_2$ of the thermal conducting material 230 from the surface temperature $T_1$ of the object, $q_{HFS}$ represents the first heat flux, $\beta_{HFS}$ and $\beta_{TH}$ represents the predefined core body temperature estimation correction coefficients.

In an example embodiment, the heat flow sensor is calibrated by using the measurement values of the thermistor pair including an insulator positioned in proximity to the heat flow sensor, and the core body temperature is estimated using the calibrated heat flow sensor, which may increase the accuracy of the estimation.

Figure 5:
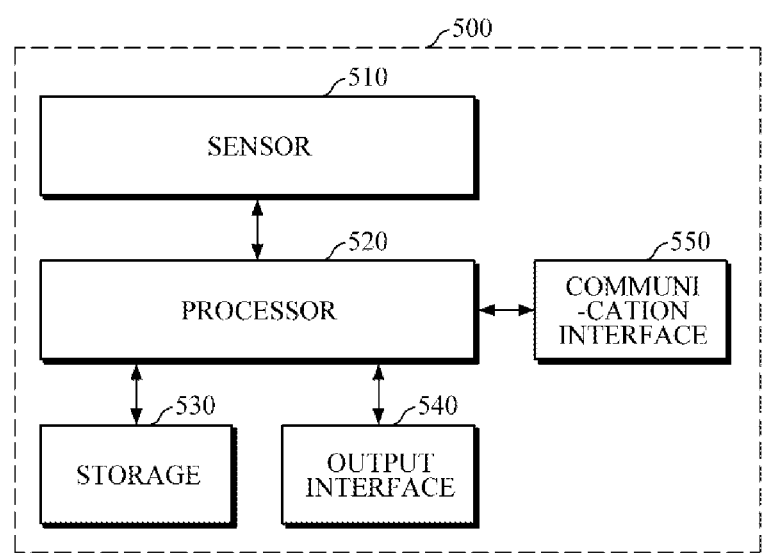
FIG. 5 is a block diagram illustrating an apparatus for estimating body temperature according to an example embodiment.

FIG. 5 is a block diagram illustrating an apparatus for estimating body temperature according to another example embodiment.

Referring to FIG. 5, an apparatus 500 for estimating body temperature may include a sensor 510, a processor 520, a storage 530, an output interface 540, and a communication interface 550. In this case, the configurations of the sensor 510 and the processor 520 are the same as or similar to those of the sensor 110 and the processor 120 of the embodiment of FIG. 1, and thus detailed descriptions thereof will not be reiterated.

The storage 530 may store information associated with core body temperature estimation. For example, the storage 530 may store a heat flux obtained through the heat flow sensor, a surface temperature of an object, a surface temperature of the thermal conducting material, a body temperature estimation model, a processing result of the processor 520, for example, a heat flux obtained using the first temperature sensor and the second temperature sensor, a correction coefficient calculated based on a ratio between a value obtained by subtracting the surface temperature of the thermal conducting material from the surface temperature of the object and the resistance value of the thermal conducting material, a calibrated heat flux, and the like.

The storage 530 may include a storage medium, such as a memory of a flash memory type, a hard disk type, a multimedia card micro type, or a card type (e.g., SD or XD memory), a random access memory (RAM), a static random access memory (SRAM), a read-only memory (ROM), an electrically erasable programmable read-only memory (EEPROM), a programmable read-only memory (PROM), a magnetic memory, a magnetic disk, an optical disk, or the like, but is not limited thereto.

The output interface 540 may provide the processing result of the processor 520 to a user. For example, the output interface 540 may display an estimated body temperature value of the processor 520 on a display. In this case, when the estimated body temperature value is outside a normal range, warning information may be provided to the user by adjusting the color or the thickness of a line for the user's easy recognition or by displaying along with the normal range. In addition, the output interface 540 may provide the estimated core body temperature value to the user through an audio output module, such as a speaker or the like, or a haptic module, together with or independently of a visual display, in a non-visual manner, such as voice, vibration, tactile sensation, or the like.

The communication interface 550 may transmit and receive various data associated with core body temperature estimation by communicating with an external device. The external device may include an information processing device, such as a smartphone, a tablet PC, a desktop PC, a notebook PC, or the like. For example, a body temperature estimation result may be transmitted to an external device, such as a user's smartphone, so that the user may manage and monitor a component analysis result through the device having a relatively superior performance.

The communication interface 550 may communicate with the external device by using various wired or wireless communication techniques such as Bluetooth communication, Bluetooth Low Energy (BLE) communication, Near Field Communication (NFC), wireless local area network (WLAN) communication, Zigbee communication, Infrared Data Association (IrDA) communication, wireless fidelity (Wi-Fi) communication, Ultra-Wideband (UWB) communication, Ant+ communication, Wi-Fi Direct (WFD) communication, Radio Frequency Identification (RFID) communication, third generation (3G) communication, fourth generation (4G) communication, fifth generation (5G) communication, and the like. However, this is merely an example and is not intended to be limiting.

Figure 6:
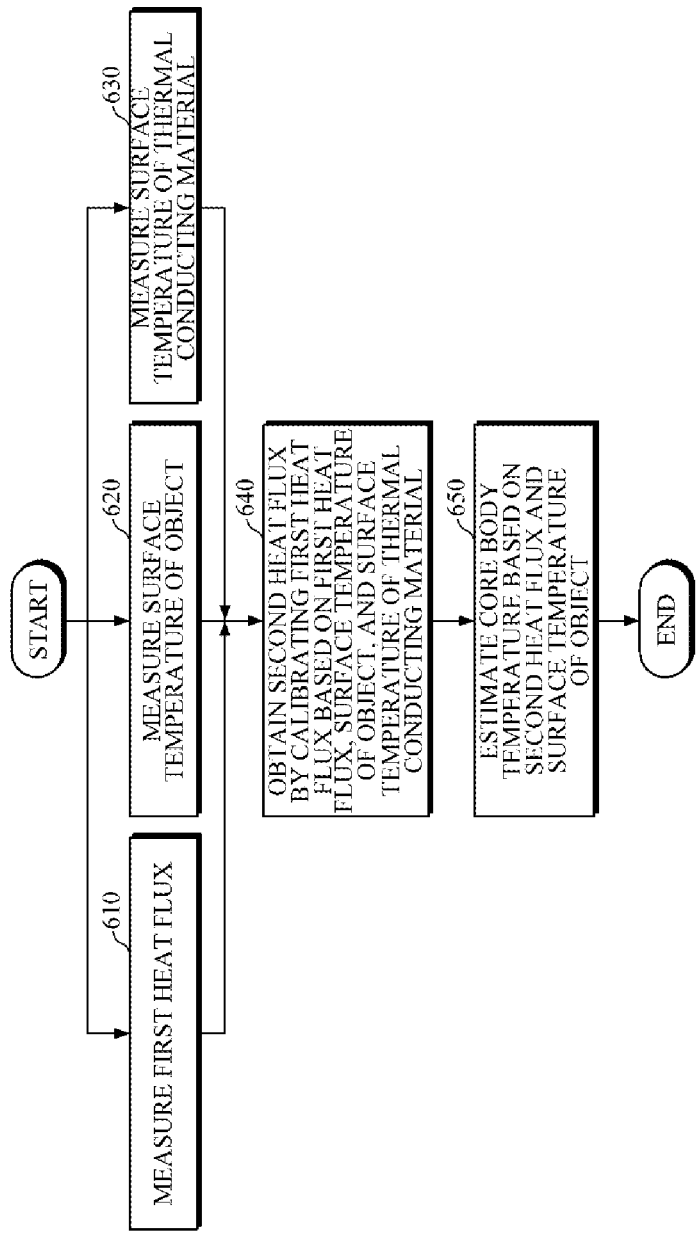
FIG. 6 is a flowchart illustrating a method of estimating body temperature according to an example embodiment.

FIG. 6 is a flowchart illustrating a method of estimating body temperature according to an example embodiment.

The method of FIG. 6 may be an example embodiment of a method of estimating body temperature performed by any one of the apparatuses 100 and 500 for estimating body temperature according to the embodiments of FIGS. 1 and 5. Hereinafter, the method will be described in brief to avoid redundancy.

Referring to FIG. 6, the apparatus for estimating body temperature may measure a first heat flux from an object through a heat flow sensor in 610.

The first temperature sensor positioned under the thermal conducting material may measure a surface temperature of the object in 620, and a second temperature sensor positioned above the thermal conducting material may measure a surface temperature of the thermal conducting material in 630. The first temperature sensor and the second temperature sensor may be disposed in a stacked manner with the thermal conducting material interposed therebetween, and may be disposed to be spaced apart from the heat flow sensor. The thermal conducting material may be an insulator, and it is also possible to fill a space between the first temperature sensor and the second temperature sensor using air having very low thermal conductivity without requiring an additional material. In addition, the first temperature sensor and the second temperature sensor may be configured as a pair of thermistors having the thermal conducting material interposed therebetween.

Next, a second heat flux may be obtained by calibrating the first heat flux based on the first heat flux, the surface temperature of the object, and the surface temperature of the thermal conducting material in 640.

For example, a first correction coefficient may be calculated based on the resistance value of the thermal conducting material, the surface temperature of the object, and the surface temperature of the thermal conducting material, and the second heat flux may be obtained by calibrating the first heat flux using the calculated first correction coefficient. In this case, the first correction coefficient may be calculated based on the ratio between a value obtained by subtracting the surface temperature of the thermal conducting material from the surface temperature of the object and the resistance value of the thermal conducting material. In addition, calibration of the first heat flux may be performed by using a value obtained by multiplying the calculated first correction coefficient and a predefined second correction coefficient.

In another example embodiment, a third heat flux may be obtained based on the surface temperature of the object and the surface temperature of the thermal conducting material, and the first heat flux may be calibrated based on the third heat flux. The third heat flux may be obtained based on the value obtained by subtracting the surface temperature of the thermal conducting material from the surface temperature of the object. In addition, a second heat flux may be obtained by combining the first heat flux and the third heat flux.

Then, the core body temperature of the object may be estimated based on the obtained second heat flux and the surface temperature of the object in 650. For example, the core body temperature of the object may be estimated based on the surface temperature of the object and the second heat flux using a predefined body temperature estimation model.

FIGS. 7 to 11 are diagrams illustrating examples of a structure of an electronic device including the apparatus 100 or 500 for estimating body temperature. The electronic device includes, but is not limited to, a smart watch, a smart band, smart glasses, a smart necklace, and an ear-type wearable device, as well as a smartphone.

Figure 7:
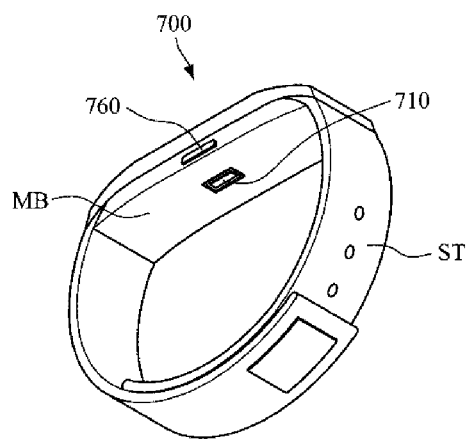
FIGS. 7 to 12 are diagrams illustrating structures of an electronic device including an apparatus for estimating body temperature according to example embodiments.

Referring to FIG. 7, an electronic device may be implemented as a smart watch type wearable device 700, and may include a main body MB and a wrist strap ST.

The main body MB may have various types of structures. A battery may be embedded in the main body MB and/or the strap ST to supply power to various configurations. The strap ST may be connected to both ends of the main body MB, enabling the main body MB to be worn on a user's wrist, and may be flexible so as to be bent around the user's wrist. The strap ST may include a first strap and a second strap separate from each other. One ends of the first strap and the second strap may be connected to each end of the main body MB and the first strap and the second strap may be fastened to each other using fastening means formed on the other sides thereof. In this case, the fastening means may be formed as Velcro fastening, pin fastening, or the like, but is not limited thereto. In addition, the strap ST may be formed as one integrated piece, such as a band, which is not separated into pieces.

The main body MB may include an apparatus for estimating body temperature. The apparatus for estimating body temperature may include a sensor 710, a processor, an output interface, a storage, and a communication interface. However, some of the display, the storage, and the communication interface may be omitted according to the size and shape of form factor.

The sensor 710 may include a heat flow sensor configured to measure a first heat flux from an object, a first temperature sensor positioned under a thermal conducting material to measure a surface temperature of the object, and a second temperature sensor positioned above the thermal conducting material to measure a surface temperature of the thermal conducting material, and may be disposed on the rear surface of the main body MB so as to obtain data to be used for core body temperature measurement from the wrist by being in contact with an upper portion of the user's wrist when the main body MB is worn on the user's wrist.

Figure 8:
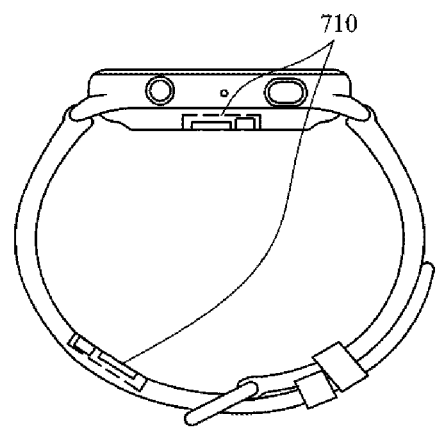

Referring to FIG. 8, the sensor 710 may be disposed not only on the rear surface of the main body MB but also on the wrist strap ST to obtain data.

Referring back to FIG. 7, a manipulator 760 may be formed on a side of the main body MB. The manipulator 760 may receive a user's command and transmit the command to the processor. The manipulator 760 may include a power button for turning on/off the wearable device 700.

The processor mounted in the main body MB may be electrically connected to various configurations including the sensor 710. The processor may estimate the core body temperature of the object using the data obtained through the plurality of sensors 710. For example, the processor may obtain a second heat flux by calibrating a first heat flux measured by a heat flow sensor based on the surface temperature of the object and the surface temperature of the thermal conducting material, and estimate the core body temperature of the object based on the obtained second heat flux and the surface temperature of the object.

A display may be provided on the front surface of the main body MB, and various application screens containing temperature information, time information, received message information, and the like may be displayed thereon. For example, an estimated core body temperature value may be displayed on the display. In this case, when the estimated body temperature value is outside a normal range, warning information may be provided to the user by using a visual indicator such as, for example, adjusting the color or the thickness of a line for the user's easy recognition or by displaying the warning information along with the normal range of a body temperature value. In addition, in an embodiment, not only a currently estimated core body temperature value but also continuously estimated core body temperature values over time may be displayed in response to a request from the user. Further, the variation in body temperature, for example, daily variation in body temperature may be shown in the form of graph, and changes in sleep state (e.g., a deep sleep state) associated with changes in body temperature may be displayed on the display.

Figure 9:
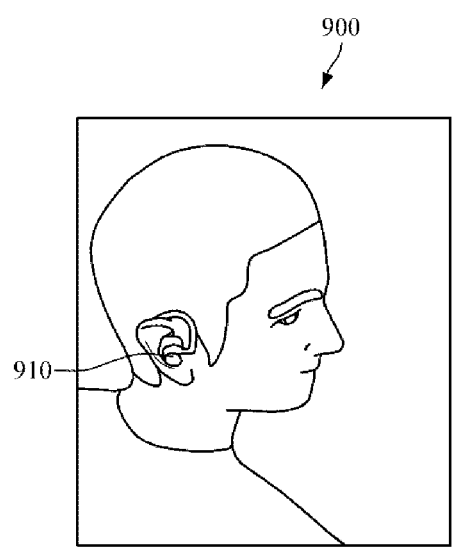

Referring to FIG. 9, the electronic device may also be implemented as an ear wearable device 900.

The ear wearable device 900 may include a main body and an ear strap. The user may wear the electronic device by wearing the ear strap on the auricle. The ear strap may be omitted depending on the shape of the ear-wearable device 900. The main body may be inserted into the external auditory meatus of the user. A sensor 910 may be mounted in the main body. The ear-wearable device 900 may acoustically provide an estimation result of body temperature to the user, or may transmit the estimation result to an external device, for example, a mobile device, a tablet device, a PC, etc. through a communication module provided in the main body.

Figure 10:
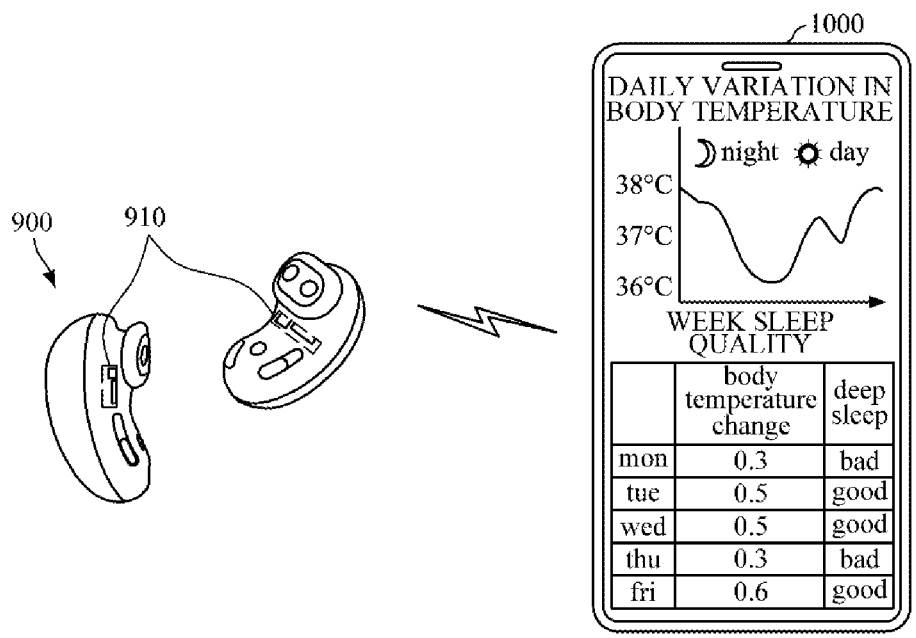

Referring to FIG. 10, the electronic device may be implemented by a combination of an ear-type wearable device and a mobile device, such as a smartphone. However, this is merely an example, and a combination of various electronic devices is possible. For example, a processor configured to estimate core body temperature may be mounted in a main body of a mobile device 1000. Upon receiving a request for estimating body temperature, the processor of the mobile device 1000 may communicate with a communication interface mounted in a main body of the wearable device 900 through a communication interface of the mobile device to control the sensor 910 to obtain data. In addition, upon receiving the data, such as heat flux, a surface temperature, etc., from the wearable device 900, the processor may estimate core body temperature and output the result on a display of the mobile device 1000 through an output interface.

Figure 11:
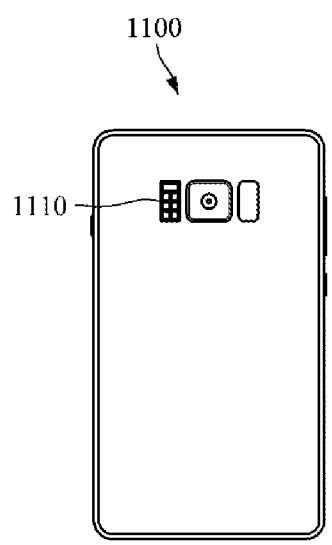

Referring to FIG. 11, the electronic device may be implemented as a mobile device 1100, such as a smartphone.

The mobile device 1100 may include a housing and a display panel. The housing may form the outer appearance of the mobile device 1100. The display panel and cover glass may be sequentially arranged on a first surface of the main body, and the display panel may be exposed to the outside through the cover glass. A sensor 1110, a camera module, and/or an infrared sensor may be disposed on a second surface of the housing.

In one embodiment, a plurality of sensors capable of acquiring data from a user may be disposed on the rear surface of the mobile device 1100, and a sensor or the like may be disposed on a fingerprint sensor of the mobile device 1100, a side power button, or a volume button, or at a separate position on the front and rear surfaces of the main body of the mobile device 1100 to estimate the core body temperature.

In addition, when the user requests estimation of body temperature by executing an application installed in the mobile device 1100, data may be obtained using the sensor 1110, the core body temperature may be estimated using a processor in the mobile device, and the estimated value may be provided to the user as an image and/or sound.

Figure 12:
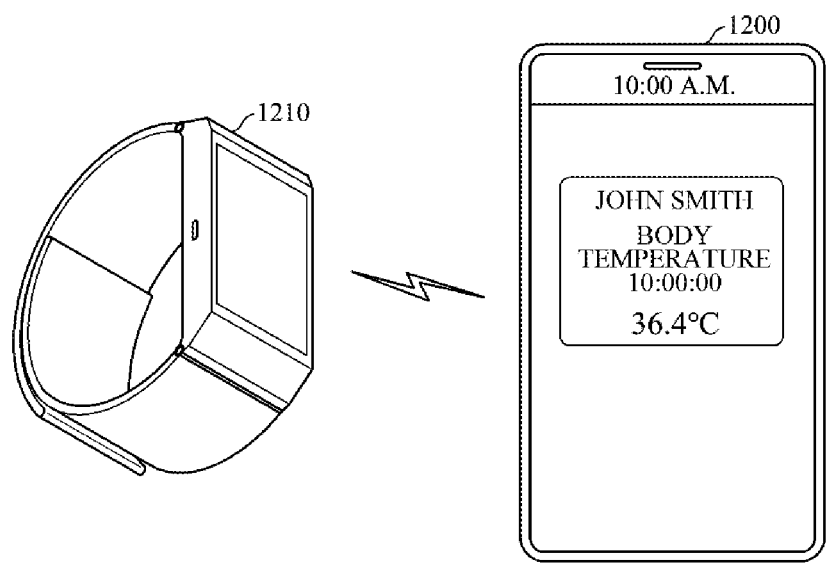

Referring to FIG. 12, the electronic device may be implemented by a combination of a watch-type wearable device and a mobile device, such as a smartphone. For example, a processor configured to estimate core body temperature may be mounted in a main body of a mobile device 1200. Upon receiving a request for estimating body temperature, the processor of the mobile device may communicate with a communication interface mounted in a main body of the wearable device 1210 through a communication interface of the mobile device to control the wearable device to obtain data. In addition, upon receiving the data, such as the heat flow velocity, a surface temperature, etc., from the wearable device, the processor may estimate core body temperature and output the result on a display of the mobile device through an output interface. In this case, not only a currently estimated core body temperature value but also continuous estimated core body temperature values over time may be displayed in response to the request from the user. Further, the variation in body temperature, for example, daily variation in body temperature may be shown in the form of graph, and changes in sleep state (e.g., a deep sleep state) associated with changes in body temperature may be displayed on the display.

The example embodiments may be implemented as computer readable codes in a computer readable record medium. Codes and code segments constituting the computer program may be easily inferred by a skilled computer programmer in the art. The computer readable record medium includes all types of record media in which computer readable data are stored. Examples of the computer readable record medium include a ROM, a RAM, a CD-ROM, a magnetic tape, a floppy disk, and an optical data storage. Further, the record medium may be implemented in the form of a carrier wave such as Internet transmission. In addition, the computer readable record medium may be distributed to computer systems over a network, in which computer readable codes may be stored and executed in a distributed manner.

At least one of the components, elements, modules or units described herein may be embodied as various numbers of hardware, software and/or firmware structures that execute respective functions described above, according to an example embodiment. For example, at least one of these components, elements or units may use a direct circuit structure, such as a memory, a processor, a logic circuit, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions, and executed by one or more microprocessors or other control apparatuses. Also, at least one of these components, elements or units may further include or implemented by a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in the block diagrams, communication between the components, elements or units may be performed through the bus. Functional aspects of the above example embodiments may be implemented in algorithms that execute on one or more processors. Furthermore, the components, elements or units represented by a block or processing operations may employ any number of related art techniques for electronics configuration, signal processing and/or control, data processing and the like.

A number of example embodiments have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus for estimating a body temperature, comprising:
a heat flow sensor configured to measure a first heat flux from an object;
a first temperature sensor positioned under a thermal insulating material and configured to measure a surface temperature of the object;
a second temperature sensor positioned above the thermal insulating material and configured to measure a surface temperature of the thermal insulating material; and
a processor configured to obtain a second heat flux by obtaining a third heat flux based on the surface temperature of the object and the surface temperature of the thermal insulating material and calibrating the first heat flux based on the third heat flux, and configured to estimate a core body temperature of the object by combining the surface temperature of the object and the second heat flux by using a predefined body temperature estimation model.

2. The apparatus of claim 1, wherein the processor is further configured to obtain a first correction coefficient based on a resistance value of the thermal insulating material, the surface temperature of the object, and the surface temperature of the thermal insulating material, and configured to calibrate the first heat flux based on the first correction coefficient.

3. The apparatus of claim 2, wherein the processor is further configured to obtain the first correction coefficient based on a ratio between a value obtained by subtracting the surface temperature of the thermal insulating material from the surface temperature of the object and the resistance value of the thermal insulating material.

4. The apparatus of claim 2, wherein the processor is further configured to calibrate the first heat flux by using a value obtained by multiplying the first correction coefficient and a predefined second correction coefficient.

5. The apparatus of claim 1, wherein the processor is further configured to obtain the third heat flux based on a value obtained by subtracting the surface temperature of the thermal insulating material from the surface temperature of the object.

6. The apparatus of claim 1, wherein the first temperature sensor and the second temperature sensor are a pair of thermistors.

7. A method of estimating a body temperature, comprising:
- measuring, by a heat flow sensor, a first heat flux from an object;
- measuring, by a first temperature sensor positioned under a thermal insulating material, a surface temperature of the object;
- measuring, by a second temperature sensor positioned above the thermal insulating material, a surface temperature of the thermal insulating material;
- obtaining a second heat flux by obtaining a third heat flux based on the surface temperature of the object and the surface temperature of the thermal insulating material, and calibrating the first heat flux based on the third heat flux; and
- estimating a core body temperature of the object by combining the surface temperature of the object and the second heat flux by using a predefined body temperature estimation model.

8. The method of claim 7, wherein the calibrating the first heat flux comprises:
- obtaining a first correction coefficient based on a resistance value of the thermal insulating material, the surface temperature of the object, and the surface temperature of the thermal insulating material; and
- calibrating the first heat flux by using the first correction coefficient.

9. The method of claim 8, wherein the obtaining the first correction coefficient comprises obtaining the first correction coefficient based on a ratio between a value obtained by subtracting the surface temperature of the thermal insulating material from the surface temperature of the object and the resistance value of the thermal insulating material.

10. The method of claim 8, wherein the calibrating the first heat flux comprises calibrating the first heat flux by using a value obtained by multiplying the first correction coefficient and a predefined second correction coefficient.

11. The method of claim 7, wherein the obtaining the third heat flux comprises obtaining the third heat flux based on a value obtained by subtracting the surface temperature of the thermal conducting insulating material from the surface temperature of the object.

12. An electronic device comprising:
- a main body; and
- an apparatus for estimating a body temperature, wherein the apparatus for estimating the body temperature comprises:
  - a heat flow sensor configured to measure a first heat flux from an object;
  - a first temperature sensor positioned under a thermal insulating material and configured to measure a surface temperature of the object;
  - a second temperature sensor positioned above the thermal insulating material and configured to measure a surface temperature of the thermal insulating material; and
  - a processor configured to obtain a second heat flux by obtaining a third heat flux based on the surface temperature of the object and the surface temperature of the thermal insulating material and calibrating the first heat flux based on the third heat flux, and configured to estimate a core body temperature of the object by combining the surface temperature of the object and the second heat flux by using a predefined body temperature estimation model.

13. The electronic device of claim 12 being a wearable device including at least one of a smart watch, a smart band, smart glasses, a smart necklace, or an ear-type wearable device.

* * * * *